United States Patent [19]
Ailhaud et al.

[11] Patent Number: 5,728,739
[45] Date of Patent: Mar. 17, 1998

[54] STIMULATING THE DIFFERENTIATION OF PREADIPOCYTIC CELLS AND THERAPIES BASED THEREON

[75] Inventors: Gérard Ailhaud; Paul Grimaldi; Irina Safonova, all of Nice; Braham Shroot, Antibes; Uwe Reichert, Pont Du Loup, all of France

[73] Assignee: Centre International De Recherches Dermatologiques Galderma, Valbonne, France

[21] Appl. No.: 510,312

[22] Filed: Aug. 2, 1995

[30] Foreign Application Priority Data

Aug. 2, 1994 [FR] France .................................. 94 09584

[51] Int. Cl.$^6$ .................................................. A61K 31/07
[52] U.S. Cl. .................. 514/725; 514/546; 514/547; 514/558; 514/559; 514/560
[58] Field of Search ............................. 514/546, 547, 514/558, 559, 560, 725

[56] References Cited

U.S. PATENT DOCUMENTS

| | | | |
|---|---|---|---|
| 4,677,120 | 6/1987 | Parish et al. | 514/549 |
| 5,246,723 | 9/1993 | Kameyama et al. | 426/549 |
| 5,278,183 | 1/1994 | Silvestrini | 514/403 |
| 5,556,844 | 9/1996 | Reichent et al. | 514/171 |
| 5,576,349 | 11/1996 | Leaf et al. | 514/559 |

FOREIGN PATENT DOCUMENTS

WO93/03713  4/1993  WIPO .

OTHER PUBLICATIONS

Proceedings Eighty–Third Annual Meeting of the American Association for Cancer Research; 33:A565–6, 1992, Sporn MB et al., "Molecular and Cellular Basis for the Use of Retinoids In Chemoprevention (Meeting Abstract)".

The New England Journal of Medicine, 329(3):177–189, 1993, Warrell, R.P. Jr. et al., "Acute promyelocytic leukemia".

Safonova et al., Fatty Acids and Retinoids Act Synergistically on Adipose Cell Differentiation (See Abstract) 1994.

*Primary Examiner*—Kevin E. Weddington
*Attorney, Agent, or Firm*—Burns, Doane, Swecker & Mathis, L.L.P.

[57] ABSTRACT

The differentiation of preadipocytic cells into adipocytic cells, in particular for correcting insulin-resistance disease states in mammalian organisms, notably in humans, for example type II diabetes and cardiovascular disorders such as hypertension and atherosclerosis, is stimulated by treating such preadipocytic cells, or a patient in need of such treatment, with an effective amount of (a) at least one ligand displaying affinity for the nuclear receptors for retinoic acid and/or isomers thereof, preferably at least one ligand displaying a specific affinity for the RAR receptors and even more preferably the RAR-α receptor and (b) at least one fatty acid, e.g., a polyunsaturated fatty acid.

16 Claims, 1 Drawing Sheet

STIMULATING THE DIFFERENTIATION OF PREADIPOCYTIC CELLS AND THERAPIES BASED THEREON

BACKGROUND OF THE INVENTION

1. Technical Field of the Invention

The present invention relates to novel pharmaceutical compositions for applications in human or veterinary medicine, intended more especially for accelerating in vitro and/or in vivo the differentiation of preadipocytic cells into adipocytic cells, and to the use of such novel compositions for correcting an insulin-resistance state existing in a living mammal, and thus of treating and/or preventing in, e.g., humans, the different physiopathologies which may be associated with such a disease state.

2. Description of the Prior Art

Certain skin cells deemed adipocytes are known to contain variable amounts of fats in the form of triglycerides. These triglycerides are synthesized in vivo actually within the adipocytes via enzymatic type reactions (lipogenesis), from free fatty acids and glucose (after degradation of the latter to glycerophosphate) in circulation in the body and supplied thereto by certain foods. In parallel, the triglycerides thus formed and then stored in the adipocyte cells may also again break down, once more under the influence of specific enzymes (lipolysis) contained in these same cells, in this instance liberating free fatty acids on the one hand and glycerol and/or glycerol mono- and/or diesters on the other. The fatty acids thus released may then either diffuse in the body and be consumed or converted via different mechanisms therein, or be taken up again (at once or a short time later) by the adipocytes to again generate triglycerides by lipogenesis.

The adipocytes present in the adipose tissue themselves originate in known manner from the transformation of precursor stem cells, designated preadipocytes, which are cells of fibroplastic appearance capable of multiplying and differentiating into adipocytes under the influence of certain hormonal agents such as, for example, insulin or growth hormone.

In humans, the amount of preadipocytes which can be isolated from the adipose tissue and which are capable of subsequently differentiating into adipocytes is inversely proportional to the individual's age; however, even in elderly individuals, there always remains a proportion of so-called "dormant" cells capable of being reactivated at a later point in time. Stated differently, throughout its life, the adipose tissue contains preadipocytes capable of differentiating into adipocytes under the influence of various appropriate stimuli. In this respect, it is known to this art that free fatty acids on the one hand, as well as, on the other, natural retinoids, when the latter are administered at physiological concentrations (1–10 nM), and synthetic retinoids when they are administered at very low concentrations (1 pM–1 nM), are, individually, good stimulators of preadipocyte differentiation.

It too is known to this art that insulin (which is a natural protein hormone produced in variable amounts by certain cells of the pancreas, known as β cells) also participates substantially, or even essentially, in the process of lipogenesis indicated above. In effect, one of the limiting parameters in the utilization by the adipocytes of the extracellular glucose contained in the body for the purpose of its ultimate conversion into triglycerides is the prior uptake, transport and diffusion of this glucose through the plasma membrane of the adipocyte cell; only glucose which has successfully permeated through this plasma membrane will be converted to glycerophosphate and then to trigtycerides. It is now known that this transport of glucose is effected by particular and fully identified glycoproteins which are located at the outer surface of the plasma membrane, and which are termed for simplicity "glucose transporters" or "GLUT". In point of fact, it is the case that certain of these GLUT (termed insulin-sensitive transporters or GLUT-4) consist, in addition, of protein receptors specific for insulin, to which (normally) the latter can become bound very firmly (creation of protein complexes of the insulin-insulin receptor type). One of the major effects of insulin being bound in this manner to these specific receptors is to produce, according to complex but known mechanisms of activation which need not be here elucidated, a significant increase in the number of GLUT at the surface of the adipocyte, thereby generating a significant increase in the amounts of glucose transported through the plasma membrane, and hence, as a result, in the amounts of triglycerides produced inside the adipocyte. In this regard, it is known that marked defects in a living organism in respect of insulin production, or, alternatively, in respect of the functioning of the insulin receptors, are responsible for various more or less serious pathologies, and in particular for a disease state referred to as sugar diabetes, more fully discussed below.

If, for various reasons (excessively rich food, inactivity, aging and the like), a substantial metabolic imbalance establishes itself in the body between the synthesis of lipids (formation of triglycerides by enzymatic reaction between fatty acids and glycerophosphate originating from glucose) and their degradation by lipolysis (enzymatic decomposition of triglycerides to fatty acids and glycerol), or, more precisely, if the amounts of fats formed by lipogenesis (the "inputs") become significantly and consistently greater than those which are removed by lipolysis (the "outputs"), an accumulation of triglycerides then occurs in the adipocytes. If this becomes excessive, it can manifest itself gradually in the appearance of a thick skin with a surface which is often irregular ("orange peel") and of more or less flabby or gelatinous consistency, finally resulting in the body having a generally unsightly appearance which can progress from simple local overweight (lipodysmorphism) through definite stoutness and ultimately to true obesity.

Obesity corresponds to a pathological state which is characterized by a generalized and substantial hypertrophy of the adipose tissue, associated with an excessive increase in both the number, the mass and the volume of the adipocytes and originating from the metabolic imbalance described above. In view of the profound discomfort, both physical and aesthetic and ofttimes psychological, it causes in the individuals who are affected, obesity is today a condition which is being less and less well endured or accepted. Furthermore and unfortunately, obesity is also often accompanied by more or less serious secondary metabolic disorders. Thus, it too is known, in particular, that obesity strongly predisposes to the early onset of certain types of sugar diabetes. Sugar diabetes, which is the sixth most common fatal disease in the United States, is defined, in general, as a pathological state of blood hyperglycemia, and, at present, two principal types of sugar diabetes are distinguishable precisely, according to the origin of this excess glucose in the blood: so-called insulin-dependent diabetes (or IDD), also termed type I diabetes, and non-insulin-dependent diabetes (or NIDD), also termed type II diabetes. As indicated above, insulin is a natural regulator of the blood glucose concentration. A deficit or ceasing of insulin production in the body causes type I diabetes;

individuals suffering from such a disease state must regularly be treated by supplementary injections of insulin. The other case corresponds to that where insulin, though present in apparently normal amounts in the body, is inactive or insufficiently active with respect to glucose, as a result of certain deficiencies regarding the functions which should be exerted by the insulin receptors; the state of the body is then qualified as insulin-resistant, and must be treated with specific antidiabetic agents.

Thiazolidinediones and derivatives thereof, and especially that having the formula:

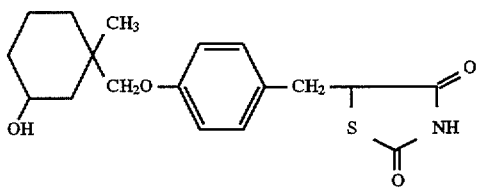

are especially valuable antidiabetic agents, recognized as enabling the state of resistance which a body may exhibit to the action of insulin to be corrected in vitro and in vivo, and useful for simultaneously stimulating the process of differentiation of preadipocytes into adipocytes.

Nonetheless, and unfortunately, one of the drawbacks of this type of compound is that, at the doses at which they are typically administered, they elicit more or less substantial undesirable side effects.

SUMMARY OF THE INVENTION

It has now unexpectedly been determined that a very substantial synergy of activity exists between certain judiciously selected compounds for activating and stimulating, markedly improvedly, the differentiation of preadipocytes into adipocytes.

Briefly, the present invention features novel pharmaceutical compositions comprising (a) a compound (or ligand) displaying an affinity for the nuclear receptors for retinoic acid and/or the isomers thereof (namely, the RAR and RXR receptors) and (b) a fatty acid, which novel compositions stimulate preadipocyte differentiation quite exceptionally.

BRIEF DESCRIPTION OF THE DRAWING

The FIGURE of Drawing is a bar graph plotting the level of differentiated preadipocytes as a function of the particular active agents employed, as well as the concentrations thereof.

DETAILED DESCRIPTION OF BEST MODE AND PREFERRED EMBODIMENTS OF THE INVENTION

Figure 1:
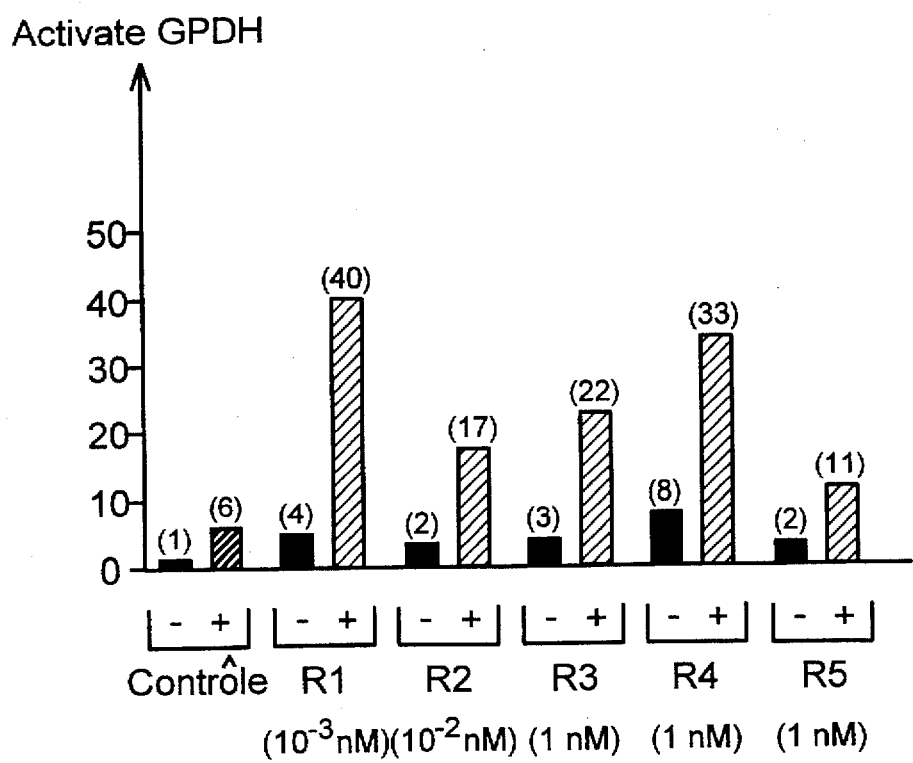

More particularly according to the present invention, optimum synergistic results are attained using compositions which comprise, preferably, a ligand specific for the RAR receptors (relative to the RXR receptors), even more preferably, a ligand specific for RARs which is, in addition, selective with respect to one or two (but preferably only one) subtypes (RAR-α, RAR-β, RAR-γ) of these RARs, and, lastly, most preferably, a ligand specific for RARs which is, in addition, selective with respect to the RAR-α receptor.

Thus, the present invention features novel compositions of matter, in particular medicinal or pharmaceutical compositions, comprising, in a vehicle, carrier or diluent which is physiologically/pharmaceutically acceptable and especially compatible with the intended mode of administration thereof, (a) at least one ligand displaying an affinity for the nuclear receptors for retinoic acid and/or isomers thereof, preferably a ligand specific for the RAR receptors and even more preferably a ligand selective for the RAR-α receptor, and (b) at least one fatty acid. The two compounds (a) and (b) can be combined physically in the composition (intimate admixture), or, to the contrary, can be present separately in different discrete compartments of appropriate packaging or dosage form (composition in the form of "kits").

The present invention thus also features multi-compartment packaging or "kits" which comprise, in a first compartment, one or more ligands displaying an affinity for the nuclear receptors for retinoic acid and/or isomers thereof, preferably a ligand specific for the RAR receptors and even more preferably a ligand selective for the RAR-α receptor, and, in a second compartment, one or more fatty acids. The active species contained in the first and second compartments are considered to be combination compositions for administration simultaneously, separately or staggered over time in a therapeutic technique for promoting and/or stimulating the differentiation of preadipocytes into adipocytes.

The subject compositions and/or kits for stimulating the differentiation of preadipocytes into adipocytes are particularly useful for the treatment of insulin-resistance states and/or associated physiopathologies.

Hence, this invention also features a therapeutic regime or regimen for stimulating the differentiation of preadipocytes into adipocytes, in particular for the treatment of insulin-resistance disease states and/or physiopathologies associated with such disease states, comprising administering to an organism in need of such treatment, preferably systemically, a therapeutically effective amount of at least one ligand displaying an affinity for the nuclear receptors for retinoic acid and/or isomers thereof, preferably a ligand specific for the RAR receptors and even more preferably a ligand selective with respect to the RAR-α receptor, and a therapeutically effective amount of at least one fatty acid. These different compounds can be administered simultaneously, separately or, alternatively, staggered over time. Preferably, they are administered simultaneously.

The compositions of the invention may of course be introduced directly into suitable cell cultures of preadipocytes (in vitro application).

In general, the unit dose amounts of active agents employed, in combination, to elicit the desired primary therapeutic effect always remain very low (synergy), which presents a considerable advantage in respect of problems of tolerance or of undesirable side effects in the organisms treated, or over the course of treatment.

In light of the exceptional activities they display with respect to the differentiation of preadipocytic cells, the compositions according to the invention are very well suited for applications in the curative and/or prophylactic treatment of patients affected by insulin resistance or by all other physiopathologies associated with this disease state. Such physiopathologies are, in particular, type II diabetes, as well as cardiovascular diseases such as, for example, hypertension and atherosclerosis. The insulin-resistance disease state in a patient may be detected conventionally via the glucose tolerance test, and the treatment according to the invention may be initiated as soon as this test proves positive, even before any clinical manifestation of an onset of disease (preventive treatment).

The various active agents according to the present invention will now be more fully described.

Specific Ligands (or Retinoids)

Retinoic acid, which is a natural metabolite of vitamin A (retinol), is known to this art as a potent modulator (i.e., an inhibitor or, to the contrary, a stimulator, depending on the nature of the cells treated) of the differentiation and proliferation of many normal or transformed cell types.

All-trans-Retinoic acid acts on the differentiation and proliferation of cells by interacting with nuclear receptors or RARs (retinoic acid receptors) contained in the cell nucleus. There are, to date, three identified subtypes of known RAR receptors, respectively termed RAR-α, RAR-β and RAR-γ. These receptors, after binding the ligand (i.e., retinoic acid), interact with the promoter region of genes regulated by retinoic acid at specific response elements. To bind to the response elements, the RARs heterodimerize with another type of receptor designated as RXR. The natural ligand of RXRs is 9-cis-retinoic acid.

Many synthetic structural analogs of retinoic acid or of 9-cis-retinoic acid, typically designated "retinoids", have, moreover, been described to date in the literature. Certain of these molecules are capable of binding and specifically activating RARs or, to the contrary, RXRs. Furthermore, certain analogs can bind and activate one particular subtype of RAR receptor (α, β or γ). Lastly, other analogs do not display any particular selective activity with respect to these different receptors. In this respect, and for example, 9-cis-retinoic acid activates both RARs and RXRs, without significant selectivity for one or the other of these receptors (nonspecific ligand), whereas all-trans- retinoic acid, in its turn, specifically activates RARs (RAR-specific ligand) without discrimination between subtypes. For the purposes of the present invention, and qualitatively, a given compound or substance (or ligand) is termed selective or specific with respect to a given family of receptors (or, respectively, with respect to a particular receptor of this family) when said substance displays a strong or very strong affinity for all of the receptors of this family (or, respectively, for the particular receptor of this family) and when it displays, moreover, a low or very low affinity for all of the receptors of any other family (or, respectively, for all other receptors, of this same family or otherwise).

Quantitatively, such affinity is measured by means of classical binding techniques (Kd values) and, according to the present invention, any compound which, with regard to a given first receptor, possesses a Kd at least 5-fold less, and preferably at least 10-fold less, than the Kd it possesses with regard to a given second receptor may be qualified as a species which is selective with respect to this first receptor relative to this second receptor; it is qualified as specific when the ratio between the said Kd values is at least 100. The evaluation of the selective or nonselective, or specific or nonspecific, character or nature of a given compound with regard to a given receptor is traditionally conducted by means of in vitro tests well known to this art (see, in particular: (1) "Selective Synthetic Ligands for Nuclear Retinoic Acid Receptor Subtypes," in *RETINOIDS*, Progress in Research and Clinical Applications, Chapter 19 (pp. 261–267). Marcel Dekker Inc. edited by Maria A. Livrea and Lester Packer; (2) "Synthetic Retinoids: Receptor Selectivity and Biological Activity" in *Pharmacol Skin*, Basel, Karger, 1993, Volume 5, pp. 117–127; (3) "Selective Synthetic Ligands for Human Nuclear Retinoic Acid Receptors," in *Skin Pharmacology*, 1992, Vol. 5, pp. 57–65; (4) "Identification of Synthetic Retinoids with Selectivity for Human Nuclear Retinoic Acid Receptor-γ," in *Biochemical and Biophysical Research Communications*, Vol. 186, No. 2, July 1992, pp. 977–983; (5) International Patent Application WO 93/21,146).

According to the present invention, of the above (natural or synthetic) retinoids, only those which display a specific affinity for the RAR receptors, i.e., ligands displaying a greater affinity for the latter receptors than for the RXR receptors, are the preferred.

In another preferred embodiment of the present invention, the RAR-specific retinoids are selected from among those which display, in addition, a selective affinity for at least one of the receptors RAR-α, RAR-β and RAR-γ, and preferably the RAR-α receptor.

It is of course possible to employ one or more ligands displaying an affinity for the nuclear receptors for retinoic acid and/or isomers thereof, or one or more ligands displaying a specific affinity with respect to the RAR receptors, or one or more ligands displaying a selective affinity with respect to the RAR-α receptor, or, alternatively, combinations from among these different ligands.

Particularly exemplary retinoids which are both BAR-specific and RAR-α-selective in accordance with this invention include 4-[(5,6,7,8-tetrahydro-5,5,8,8-tetramethyl-2-naphthyl) carboxamido]benzoic acid and 4-[(5,6,7,8-tetrahydro-5,5,8,8-tetramethyl-2-naphthyl)carbamoyl] benzoic acid.

Particularly exemplary retinoids specific for RAR include all-trans-retinoic acid, 4-(5,6,7,8-tetrahydro-5,5,8,8-tetramethyl-2-anthracenyl)benzoic acid, 4-[(5,6,7,8-tetrahydro-5,5,8,8-tetramethyl-2-naphthyl)carboxamido] benzoic acid, 6-[3-(1-adamantyl)-4-hydroxyphenyl]-2-naphthoic acid, 6-[3-(1-methylcyclohexyl)-4-methoxyphenyl]-2-naphthoic acid and adapalene.

Fatty Acids

The fatty acids which are suitable according to the present invention can be saturated or, to the contrary, unsaturated fatty acids. Among the latter, preferred are the polyunsaturated fatty acids, and especially polyunsaturated $C_{18}$–$C_{22}$ fatty acids (including the so-called "essential" fatty acids), and in particular the $C_{20}$ acids. The subject fatty acids, in addition, can also be metabolizable or non- metabolizable. Fatty acid precursors can also be employed, namely, compounds which are metabolized in vivo by the body into fatty acids, or, alternatively, compounds which induce the formation of polyunsaturated fatty acids in living tissue. This can be established objectively by gas chromatography or by any other standard technique such as those described by Pelick et al. P23 "Analysis of lipids and lipoproteins", Perkins American Oil Chemist Society editions, Champaign Ill., U.S.A.

Exemplary fatty acids which are particularly well suited according to the present invention include arachidonic acid, dihomo-gamma-linolenic acid, eicosapentaenoic acid, docosahexaenoic acid and oleic, linoleic, α-linolenic and γ-linolenic acids, as well as palmitic and, especially, α-bromopalmitic acid.

In a preferred embodiment of the invention, the fatty acids are selected from among the $\omega_3$ and $\omega_6$ type polyunsaturated fatty acids. Particularly preferred such fatty acids are α-linolenic acid and arachidonic acid.

The above indicated fatty acids (or precursors thereof) may be obtained, in particular, from certain natural materials, especially from certain foods of animal, vegetable or microbial origin (extracts of vegetable oils such as Oenothera biennis oil, borage oil, blackcurrant-pip oil, evening primrose oil, fish oil extracts and extracts of insect tissue oils). According to the invention, it is of course also intended to directly use such natural materials which contain the desired fatty acids or fatty acid precursors. It is also possible to use synthetic products. Lastly, it will also be appreciated that it is obviously intended to employ mixtures of fatty acids.

In general, the retinoids and the fatty acids in accordance with the present invention may be packaged conventionally in a form suited to the mode of administration or application ultimately selected for these compounds. The compositions according to the invention may thus be administered enterally, parenterally or, alternatively, transcutaneously or transdermally (with or without the use of penetration promoter(s)). However, preferably, the subject compositions are formulated in a form suitable for enteral application.

The preferred compositions according to the present invention are pharmaceutical compositions comprising, in a physiologically/pharmaceutically acceptable vehicle, carrier or diluent, at least one retinoid specific for the RAR receptors, and which is more preferably, in addition, selective for the RAR-α receptor, as a first active principle, in intimate admixture with at least one fatty acid present as a second active principle. These compositions are preferably formulated and packaged in a form suitable for systemic administration and, even more preferably, for oral administration. This is also the case in respect of the "kits" according to the invention; in particular, the compositions included in each of the compartments of the kit are preferably formulated in a form suitable for systemic, advantageously oral administration. It should also be appreciated that kits can be designed containing the same number of separate compartments as active species (retinoids, fatty acids) in the intended final composition.

For enteral administration, the medicinal/pharmaceutical compositions of the invention can be formulated as tablets, hard gelatin capsules, dragees, syrups, suspensions, solutions, powders, granules, emulsions, microspheres or nanospheres, or lipid or polymeric vesicles permitting a controlled release thereof.

For parental administration, the subject medicinal/pharmaceutical compositions can be formulated as solutions or suspensions for perfusion or for injection.

The compositions according to the invention, or the kits comprising same, can also include any of the various excipients and other traditional additives and adjuvants which are typically employed in the pharmacopoeia or pharmaceutical arts (colorants, texturizing agents, perfumes, fragrances, preservatives and the like).

The amounts of the specific retinoid(s) employed according to the present invention are not strictly critical, and can thus vary over fairly wide limits. In the instance of preparations intended for systemic administration, the dose amounts must remain compatible with the traditional requirements associated with the toxicology and formulation of pharmaceuticals; in this respect, administration doses ranging from 0.005 mg/kg/day to 5 mg/kg/day are generally suitable.

Similarly, the amounts of fatty acid(s) to be administered generally range from 1 mg/kg/day to 50 mg/kg/day.

To elicit significant therapeutic effects, the frequencies or regimen of administration of the compositions according to the invention, which are of course dependent on the amounts of active agents employed at each application, are on the order of once to twice daily. The therapy is then continued regularly for several days and, preferably, for several weeks or even several months.

In order to further illustrate the present invention and the advantages thereof, the following specific examples are given, it being understood that same are intended only as illustrative and in nowise limitative.

EXAMPLE 1

This example demonstrates the in vitro activity of the synergistic immixtures according to the invention with respect to the differentiation of preadipocytic cells into adipocytic cells.

The compounds tested were the following:

Retinoids

R1: 4-(5,6,7,8-tetrahydro-5,5,8,8-tetramethyl-2-anthracenyl)benzoic acid (RAR-specific retinoid, without particular selectivity for α, β or γ subtypes);

R2: 4-[(5,6,7,8-tetrahydro-5,5,8,8-tetramethyl-2-naphthyl)carboxamido]benzoic acid (RAR-specific retinoid selective for RAR-α);

R3: 6-[3-(1-methylcyclohexyl)-4-methoxhenyl]-2-naphthoic acid (RAR-specific and RAR-β-selective retinoid);

R4: 6-[3-(1-adamantyl)-4-hydroxyphenyl]-2-naphthoic acid (RAR-specific and RAR-γ-selective retinoid);

R5: 9-cis-retinoic acid (nonspecific retinoid).

Fatty Acid

α-Bromopalmitic acid.

The preadipocytic cells used were cells originating from the line Ob1771.

The experimental protocol and the methods of determination of the differentiation activities were as follows:

Cell Culture

Cells were cultured at 37° C. in a humid atmosphere in the presence of 5% of $CO_2$ in DME medium (Gibco) with the addition of antibiotics (penicillin 100 U/ml and streptomycin 50 mg/ml) and 8% (v/v) of fetal calf serum (FCS) (standard medium).

Treatment Of Cells

Ob 1771 cells were inoculated in the proportion of $2 \times 10^4$ cells in 2 ml of standard medium with the addition of 17 mM insulin, 2 nM triiodothyronine, 100 μM putrescine and 10 μM methylglyoxal bis(guanylhydrazone) in 10 $cm^2$ cluster wells. The cells were treated immediately after inoculation with the retinoids indicated above and/or α-bromopalmitic acid, both diluted in ethanol. The final ethanol concentration did not exceed 0.1% (v/v). After 8 days of culture, the cells were harvested for the determination of differentiation.

Measurement of Differentiation

Differentiation was determined by means of the glycerophosphate dehydrogenase (GPDH) activity measured spectrophotometrically at 340 nm. It is expressed in mU (μmol/min)/mg of protein. The stronger the activity, the higher the proportion of differentiated cells. The results are expressed relative to the activity determined in cells not exposed to the retinoids and/or the fatty acid (35±5 mU/mg).

All of the results obtained are reported in the Figure of Drawing. This Figure quantifies the changes in the level of differentiated preadipocytes as a function of the active agents used, on the one hand, and of their concentration on the other (R1:10$^{-3}$ nM; R2:10$^{-2}$ nM; R3:1 nM; R4:1 nM; R5:1 nM). In all cases, the concentration of fatty acid (when present) was fixed at 5 µM; (+) indicates the presence of this fatty acid and (−) its absence. The values given at the control point correspond to the results found when no retinoid was employed (in the latter case, (−) corresponds to the values found when no active agent was employed (absence of fatty acid) and (+) to those found on employing only the fatty acid at a concentration of 5 µM).

These results clearly demonstrate the synergistic effects elicited by use of the combinations according to the invention, the amount of differentiated cells being, in effect, consistently greater than the simple arithmetic sum of the amounts of differentiated cells obtained when the retinoids and the fatty acid were employed separately and in isolation.

EXAMPLE 2

Three specific formulations according to the invention, and which are in a form suitable for oral administration, are set forth in this example.

(a) 1 g capsule containing 0.5 g of an oily suspension comprising:

| (i) | Compound R1 of Example 1 | | 0.25 mg |
|---|---|---|---|
| (ii) | α-Linoleic acid | | 250 mg |
| (iii) | Liquid paraffin | qs | 500 mg |

The shell of the capsule was manufactured according to a conventional technique of molding and then drying a suitable mixture comprising: gelatin, glycerol, water and preservative. The operations of mixing and then of withdrawing the ingredients constituting the oily suspension were carried out under an inert gas.

(b) 0.30 ml hard gelatin capsule (opaque M°3 calibrated standard shell) containing:

| (i) | Adapalene | | 5 mg |
|---|---|---|---|
| (ii) | α-Bromopalmitic acid | | 50 mg |
| (iii) | Silica ("AEROSIL 200" marketed by Degussa) | | 50 mg |
| (iv) | Lactose | qs | 0.3 ml |

(c) 0.5 g insoluble tablet comprising:

| (i) | Compound R2 of Example 1 | | 2.5 mg |
|---|---|---|---|
| (ii) | α-Bromopalmitic acid | | 100 mg |
| (iii) | Lactose | | 85 mg |
| (iv) | Purified talc | | 15 mg |
| (v) | Sweetener | qs | |
| (vi) | Colorant | qs | |
| (vii) | Starch | qs | 500 mg |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A composition of matter suited for the differentiation of preadipocytic cells into adipocytic cells, comprising (a) at least one ligand displaying affinity for the nuclear receptors for retinoic acid and/or isomers thereof, and (b) at least one fatty acid.

2. The composition of matter as defined by claim 1, said at least one ligand (a) comprising a ligand displaying a specific affinity for the RAR receptors.

3. The composition of matter as defined by claim 2, said at least one RAR-specific ligand (a) not displaying selective affinity for one of the subtypes of RAR receptors.

4. The composition of matter as defined by claim 2, said at least one ligand (a) displaying a specific affinity for the RAR receptors also displaying a selective affinity for at least one of the subtypes of RAR receptors.

5. The composition of matter as defined by claim 4, said at least one of the subtypes of RAR receptors comprising the RARα receptor.

6. The composition of matter as defined by claim 1, said at least one ligand (a) comprising 4-[(5,6,7,8-tetrahydro-5,5,8,8-tetramethyl-2-naphthyl)carboxamido]benzoic acid, 4-[(5,6,7,8-tetrahydro-5,5,8,8-tetramethyl-2-naphthyl)carbamoyl]benzoic acid, all-trans-retinoic acid, 4-(5,6,7,8-tetrahydro-5,5,8,8-tetramethyl-2-anthracenyl)benzoic acid, 4-[(5,6,7,8-tetrahydro-5,5,8,8-tetramethyl-2-naphthyl)carboxamido]benzoic acid, 6-[3-(1-adamantyl)4-hydroxyphenyl]-2-naphthoic acid, 6-[3-(1-methylcyclohexyl)-4-methoxyphenyl]-2-naphthoic acid or adapalene.

7. The composition of matter as defined by claim 1, said at least one fatty acid (b) comprising a saturated or unsaturated fatty acid.

8. The composition of matter as defined by claim 7, said at least one fatty acid (b) comprising a polyunsaturated fatty acid.

9. The composition of matter as defined by claim 8, said polyunsaturated fatty acid having from 18 to 22 carbon atoms.

10. The composition of matter as defined by claim 8, said polyunsaturated fatty acid being of $W_3$ or $W_6$ type.

11. The composition of matter as defined by claim 1, said at least one fatty acid (b) comprising arachidonic acid, dihomo-gamma-linolenic acid, eicosapentaenoic acid, docosahexaenoic acid, oleic acid, linoleic acid, α-linolenic acid, γ-linolenic acid, palmitic acid or α-bromopalmitic acid.

12. The composition of matter as defined by claim 1, further comprising a physiologically/pharmaceutically acceptable vehicle, carrier or diluent therefor.

13. The composition of matter as defined by claim 12, formulated for enteral administration to a mammalian organism.

14. The composition of matter as defined by claim 12, formulated for parenteral administration to a mammalian organism.

15. The composition of matter as defined by claim 12, formulated for transcutaneous administration to a mammalian organism.

16. The composition of matter as defined by claim 12, comprising a tablet, hard gelatin capsule, dragée syrup, suspension, solution, powder, granules, emulesion, microspheres or nanospheres, or liquid or polymeric vesicles for controlled release.

* * * * *